United States Patent [19]
Beckmann et al.

[11] Patent Number: 5,777,089
[45] Date of Patent: Jul. 7, 1998

[54] PHENOL DERIVATIVES, THEIR PREPARATION AND THEIR USE, IN PARTICULAR IN NONLINEAR OPTICS

[75] Inventors: Stefan Beckmann, Bad Dürkheim; Karl-Heinz Etzbach, Frankenthal; Rüdiger Sens, Mannheim, all of Germany

[73] Assignee: BASF Aktiengesellschaft, Ludwigshafen, Germany

[21] Appl. No.: 722,141

[22] PCT Filed: Apr. 7, 1995

[86] PCT No.: PCT/EP95/01290

§ 371 Date: Oct. 15, 1996

§ 102(e) Date: Oct. 15, 1996

[87] PCT Pub. No.: WO95/28396

PCT Pub. Date: Oct. 26, 1995

[30] Foreign Application Priority Data

Apr. 15, 1994 [DE] Germany .................. 44 12 983.1

[51] Int. Cl.$^6$ .............. C09B 29/033; C09B 29/042; C07D 333/38; G02F 1/35
[52] U.S. Cl. .............. 534/765; 534/775; 534/791; 534/794; 548/193; 548/194; 549/61; 549/68; 8/691; 8/662; 106/31.45; 106/31.5; 106/31.51; 385/130; 359/321
[58] Field of Search .............. 548/193; 549/61, 549/68; 534/765, 775, 791, 794; 385/130; 359/321; 8/691, 662; 106/31.45, 31.5, 31.51

[56] References Cited

U.S. PATENT DOCUMENTS

| | | | |
|---|---|---|---|
| 1,743,083 | 1/1930 | Johnson | 548/193 |
| 4,668,775 | 5/1987 | Bergmann et al. | 534/765 |
| 5,188,641 | 2/1993 | Parton | 8/647 |
| 5,290,630 | 3/1994 | Devonald et al. | 428/333 |

FOREIGN PATENT DOCUMENTS 0 205 069 A2  12/1986  European Pat. Off. .
0 493 716 A1   7/1992  European Pat. Off. .

OTHER PUBLICATIONS

Bizhev et al., Chemical Abstracts, 108:180074 (1988).
Blokhin et al., Chemical Abstracts, 101:23985 (1984).
Nath et al., Chemical Abstracts, 95:187135 (1981)
Agrawal et al., Chemical Abstracts, 95:150521 (1981).
Choudhari et al., Chemical Abstracts, 89:215283 (1978).
Chaaban et al., Chemical Abstracs, 101:72657 (1984).
Mahapatra, Chemical Abstracts, 52:9079e (1958).
Okamiya, Chemical Abstracts, 55:5471 (1961).
Sen et al., Chemical Abstracts, 55:1581i (1961).
Organic Polymeric and Non–Polymeric Materials with Large Optical Nonlinearities Angew. Chem. Int. Ed. Engl. 23(1984) pp. 690–703 By David J. Williams.
Z. Naturforschg. 20a, (1965) pp. 1441–1471, W. Liptay.
Journal Original Chemical, 1989, 54, 3774–3778, M.S. Paley, et al., "A Solvatochromic Method for Determining Second–Order Polarizabilities of Organic Molecules".
Electro–Optices, "Polymers for Non–linear Optical Devices", C. Jones, Oct., 1990, pp. 600–608.

*Primary Examiner*—Fiona T. Powers
*Attorney, Agent, or Firm*—Oblon, Spivak, McClelland, Maier & Neustadt, P.C.

[57] ABSTRACT

Phenol derivatives of the general formula I

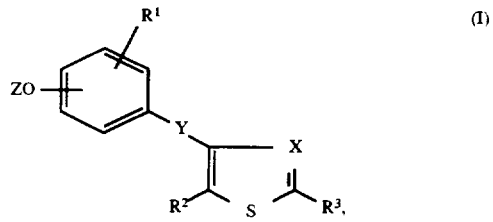

(I)

where $R^1$, $R^2$, $R^3$, X, Y and Z have the meanings stated in the description, are used in particular in nonlinear optics.

11 Claims, No Drawings

PHENOL DERIVATIVES, THEIR PREPARATION AND THEIR USE, IN PARTICULAR IN NONLINEAR OPTICS

This application is a 371 of PCT/EP95/01290 filed Apr. 7, 1995.

BACKGROUND OF THE INVENTION

1. Field of the Invention

The present invention relates to phenol derivatives, processes for their preparation, polymers which contain these phenol derivatives as monomers and their use, in particular in nonlinear optics.

2. Discussion of the Invention

The nonlinear optical properties of organic compounds are utilized in many areas of optoelectronics. Examples of this are applications in frequency doubling, phase modulators, optical amplifiers, interferometers or optical switches and communications engineering.

It is generally known that organic materials, in particular polymers having special chromophores, may have nonlinear optical properties which in some cases are more pronounced than those of comparable inorganic materials.

The most frequently used materials at present are inorganic crystals, for example those of potassium dihydrogen phosphate or lithium niobate. These crystals are prepared by a complicated and expensive process and, owing to their rigid structure, can be used in optical apparatuses only with difficulty.

One particular advantage of suitable organic chromophores and their use in polymeric materials is their simple preparation and processing.

The chromophores used in nonlinear optics are employed as a rule in either crystalline or polymer-bound form.

Angew. Chem., 96 (1984), 637–651 discloses the use of stilbene derivatives or special azo dyes for this purpose.

SUMMARY OF THE INVENTION

It is an object of the present invention to provide suitable phenol derivatives which are advantageous in particular for use in polymeric nonlinear optical systems. In particular, these phenol derivatives or dyes which can be derived therefrom should have large hyperpolarizability values, good heat stability, good compatibility with the polymers used in nonlinear optical systems and good film formation properties with copolymers.

We have found that this object is achieved by phenol derivatives of the general formula I

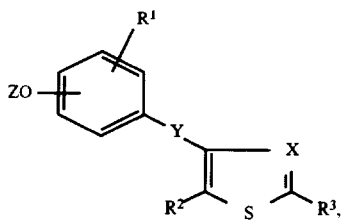
(I)

where $R^1$ and $R^2$, independently of one another, are hydrogen, $C_1$–$C_{10}$-alkyl, $C_3$–$C_8$-cycloalkyl, $C_1$–$C_{10}$-alkoxy, OH, $NR^5R^6$, CN, $NO_2$, halogen, CHO,

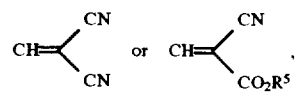

X is N or $CR^4$,

Y is a chemical bond, S,

$SO_2$, O or $NR^6$,

Z is hydrogen, acryloyl or methacryloyl, $R^3$ is $NH_2$, N=N—G, where G is a heterocyclic coupling component, or

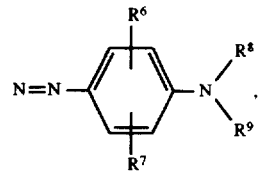

$R^4$ is hydrogen, CN, $NO_2$ or $CO_2R^5$, $R^5$ is hydrogen, alkyl, cycloalkyl, unsubstituted or substituted phenyl, benzyl or alkoxy, $R^6$ and $R^7$, independently of one another, are each hydrogen, $C_1$–$C_{10}$-alkyl, $C_3$–$C_8$-cycloalkyl or $C_1$–$C_6$-alkoxy which is unsubstituted or substituted by phenyl or by $C_1$–$C_4$-alkoxy, and $R^8$ and $R^9$ are each hydrogen, alkyl, cycloalkyl or a crosslinkable group, where $R^8$ and $R^9$ together with the nitrogen atom linking them may form a ring.

The present invention furthermore relates to a process for the preparation of certain phenol derivatives, and the use of these phenol derivatives in nonlinear optics, for coloring textiles or for thermal transfer printing.

DETAILED DESCRIPTION OF THE PREFERRED EMBODIMENTS

Phenol derivatives of the formula I, where Y is a chemical bond and/or X is $CR^4$, are particularly suitable according to the invention.

Phenol derivatives of the formula I, where $R^1$ is hydrogen, $C_1$–$C_{10}$-alkyl, $C_3$–$C_8$-cycloalkyl, $C_1$–$C_{10}$-alkoxy, OH, halogen or CHO and $R^2$ is hydrogen, CN, $NO_2$, CHO,

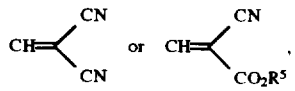

are also particularly suitable according to the invention.

In a preferred embodiment of the invention, $R^3$ is $NH_2$. Very particularly preferred phenol derivatives are of the formula II

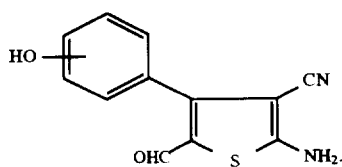
(II)

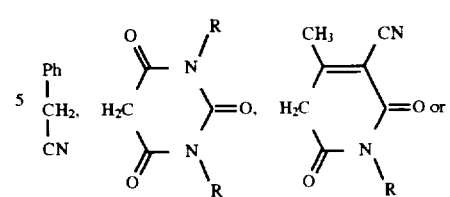

These compounds are particularly suitable as intermediates for the preparation of novel phenol derivatives of the formula I, where $R^3$ is

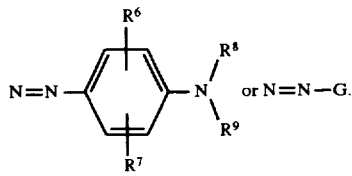

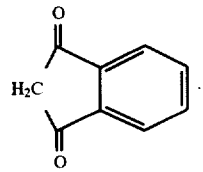

These are directly useful for applications in nonlinear optics.
Suitable radicals G are, for example,

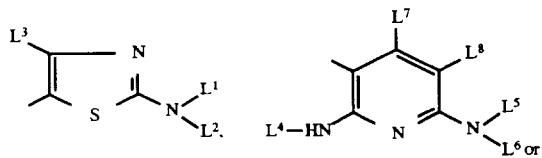

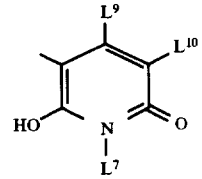

where
- $L^1$ and $L^2$ are identical or different and, independently of one another are each hydrogen or unsubstituted or substituted $C_1$–$C_6$-alkyl which may be interrupted by 1 or 2 ether oxygen atoms, or are each $C_5$–$C_7$-cycloalkyl or $C_3$–$C_6$-alkyl.
- $L^3$ is hydrogen, $C_1$–$C_{12}$-alkyl, unsubstituted or substituted phenyl or thienyl.
- $L^4$, $L^5$ and $L^6$ are identical or different and, independently of one another, are each unsubstituted or substituted $C_1$–$C_{12}$-alkyl which may be interrupted by from 1 to 3 ether oxygen atoms,
  - $C_5$–$C_7$-cycloalkyl, unsubstituted or substituted phenyl, $C_3$–$C_6$-alkenyl, unsubstituted or substituted benzoyl, $C_1$–$C_8$-alkanoyl, $C_1$–$C_6$-alkylsulfonyl or unsubstituted or substituted phenylsulfonyl, or $L^5$ and $L^6$ together with the nitrogen linking them are a 5- or 6-membered saturated heterocyclic radical which may contain further heteroatoms.
- $L^7$ is hydrogen or $C_1$–$C_6$-alkyl.
- $L^8$ is cyano, carbamoyl or acetyl.
- $L^9$ is hydrogen or $C_1$–$C_6$-alkyl and
- $L^{10}$ is cyano, carbamoyl or acetyl.

In addition to hydrogen, CN, $NO_2$ and $CO_2R^5$, where $R^5$ is hydrogen, alkyl, cycloalkyl, unsubstituted or substituted phenyl, benzyl, alkoxy, $R^4$ may, if required, also be a radical of another CH-acidic compound, for example The phenol derivatives 1 to 16 are particularly preferred according to the invention.

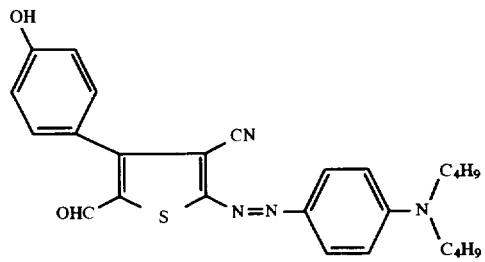

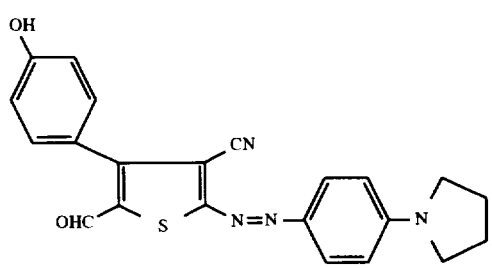

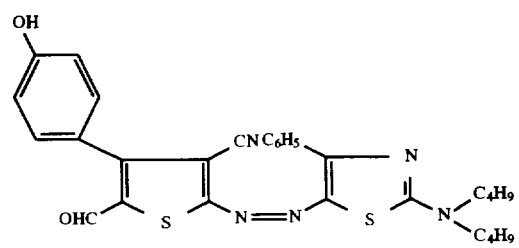

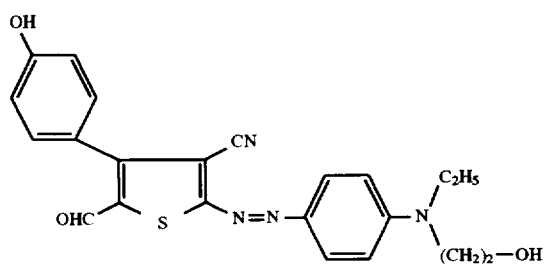

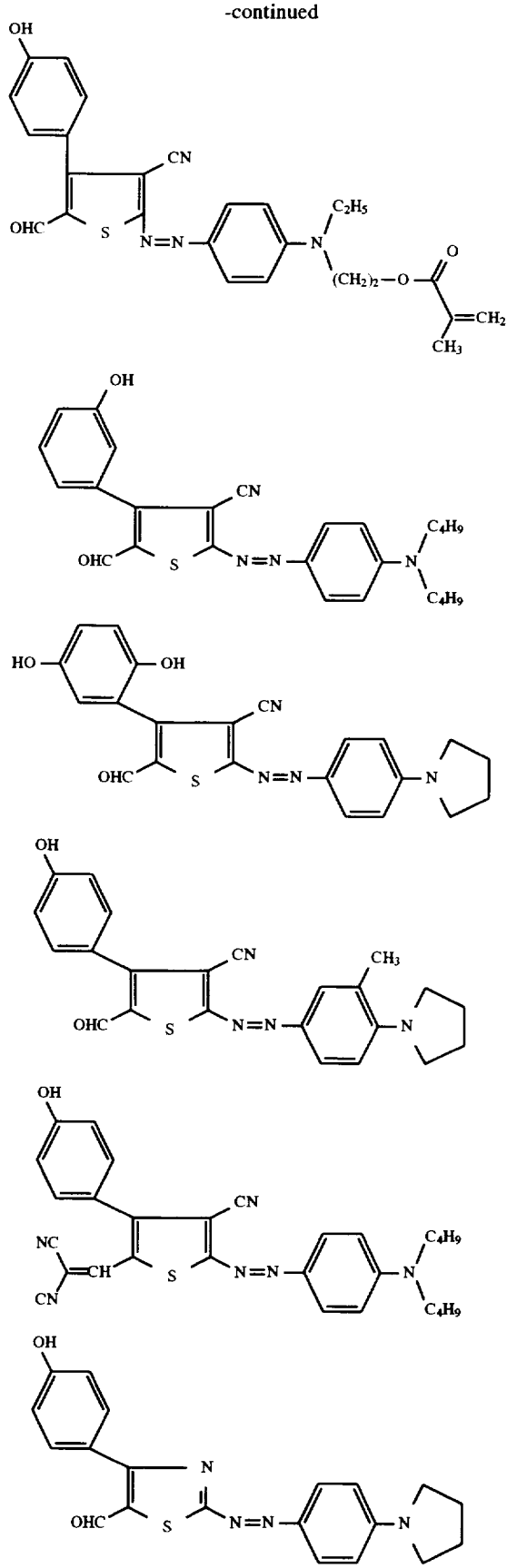
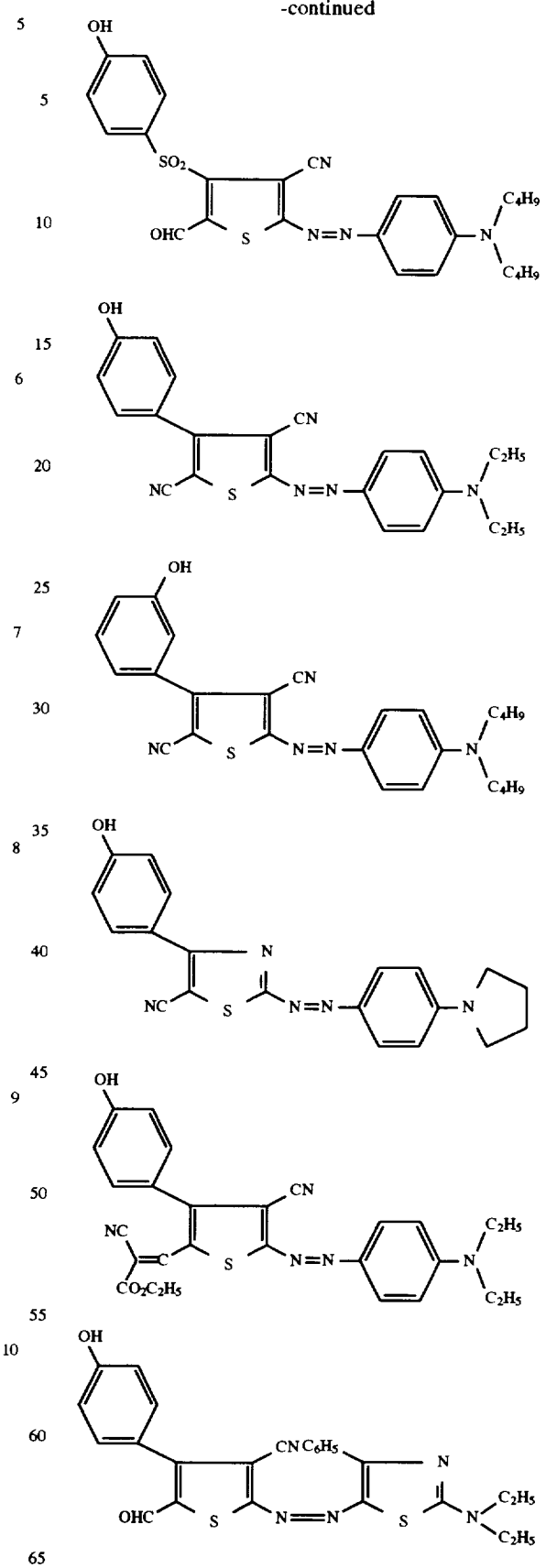
Among these, the dyes 1, 4, 5, 9, 12 and 13 are particularly preferred.

The present invention also relates to polymers which contain these phenol derivatives as monomers. The phenol derivatives are preferably used here in the form of the corresponding acrylates and methacrylates.

The novel phenol derivatives are obtainable in a manner known per se. For example, phenol derivatives of the formula I where $R^3$ is N=N—G or

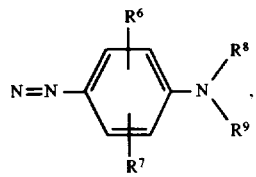

can be prepared by diazotizing phenol derivatives of the formula I where $R^3$ is $NH_2$ in a manner known per se and reacting the product with a heterocyclic coupling component G or with

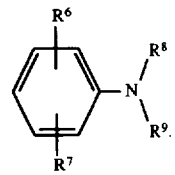

The novel compounds are thermally stable and have particularly large molecular hyperpolarizability values of (β). Moreover, the dyes have good compatibility with the polymers used in nonlinear optical systems and good film formation properties in copolymers.

The molecular hyperpolarizability can be determined, for example, by the method for measuring the solvatochromism (cf. for example Z. Naturforschung, 20a (1965), 1441–1471, or J. Org. Chem. 54 (1989), 3775–3778). In this method, the position of the absorption band of a compound is determined in different solvents, for example in dioxane or dimethyl sulfoxide. The shift of the absorption band is then directly proportional to the β-value ie. compounds having a large solvatochromic shift have a large molecular hyperpolarizability and are therefore suitable for use in nonlinear optical systems (cf. for example Chemistry and Industry, Oct. 1, 1990, pages 600 to 608).

The suitability of the novel substances in communications engineering, in electrooptical modulators (eg. Mach-Zehnder interferometer), in optical switches, in frequency mixing or in optical waveguides is particularly noteworthy here.

The examples which follow illustrate the invention.

EXAMPLES

In the examples which follow, percentages and ratios are by weight.

In Examples 1 to 16, phenol derivatives 1 to 16 were prepared. For the phenol derivatives 1 to 3, the solvatochromism was determined as a measure of the property of the hyperpolarizability, which is important in nonlinear optics.

Example 1
Preparation of 1

For the preparation of 1, 1a was first prepared starting from 4-hydroxyacetophenone. The compounds 1b, 1c, 1d and finally 1 were then prepared from 1a in further steps.

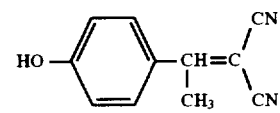

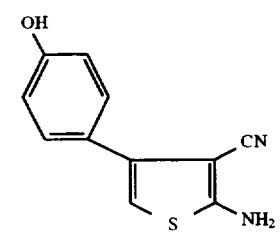

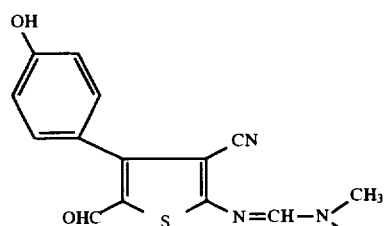

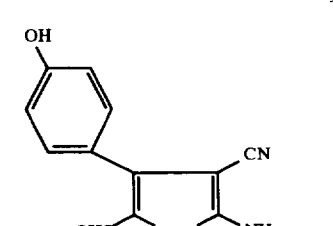

Preparation of 1a 244.8 g (1.8 mol) of 4-hydroxyacetophenone were heated at the boil under a water separator with the addition of 540 ml of toluene, 118.9 g (1.8 mol) of malodinitrile, 16.04 g (0.18 mol) of β-alanine and 21.6 g of glacial acetic acid for 4.5 hours. After cooling, the precipitate formed was filtered off with suction, washed with 500 ml of water and dried at 50° C. under reduced pressure.

Yield: 297.9 g

Melting point: 116°–117° C.

Preparation of 1b 161.7 g (0.88 mol) of 1a were dissolved in 880 ml of ethanol and the solution was added dropwise to a boiling solution of 28.3 g (0.88 mol) of sulfur and 79.2 g of (0.91 mol) of morpholine in 880 ml of ethanol. Thereafter, the mixture was heated at the boil for a further 1.5 hours. After cooling to 50° C., the reaction batch was added to 1000 ml of an ice/water mixture and the product was filtered off with suction, washed with 500 ml of water and dried at 50° C under reduced pressure.

Yield: 164.6 g

Melting point: 205°–206° C.

Preparation of 1c 86.4 g (0.4 mol) of 1b were dissolved in 860 ml of dimethylformamide, and 201.46 g (1.32 mol) of phosphory chloride were added at 5° C. Thereafter, stirring was carried out for 1.5 hours at 70° C. and the reaction mixture was added to 5000 ml of an ice/water mixture. The precipitate formed was filtered off with suction, washed with 1 l of water and dried at 50° C. under reduced pressure.

Yield: 107.6 g

Melting point: 230° C.

Preparation of 1d 44.8 g (0.15 mol) of 1c in 440 g of 50% formic acid were heated at the boil for 7 hours. After cooling, the precipitate formed was filtered off with suction, washed with 500 ml of water and dried at 50° C. under reduced pressure.

Yield: 41.9 g

Melting point: 280° C.

Preparation of 1

7.32 g (0.03 mol) of 1d were suspended in 120 ml of phosphoric acid (85% strength), and 9.45 g (0.03 mol) of nitrosylsulfuric acid were added at from 0° to 5° C. After a further 3 hours at 5° C., the suspension was added to a solution of 6.71 g (0.03 mol) of N,N-dibutylaniline in 200 ml of hydrochloric acid and 50 ml of methyl tert-butyl ether. After a further 12 hours at 20° C., the precipitate formed was filtered off with suction, washed with 500 ml of water and dried at 20° C. The product was then purified by means of column chromatography over silica gel (4:1 tetrahydrofuran/toluene) and then recrystallized from toluene.

Yield: 3.7 g

Melting point: 210°–211° C.

UV(CH$_2$Cl$_2$): $\lambda_{max}$=587 nm. $\epsilon$=59200.

Elemental analysis (calculated for C$_{20}$H$_{28}$N$_4$O$_2$S): calculated: C 67.8 H 6.13 O 6.94 N 12.16 S 6.9 found C: 67.30 H 6.04 O 7.72 N 11.85 S 7.3

Example 2

Preparation of 2

17.8 g (0.073 mol) of compound 1d were diazotized with nitrosylsulfuric acid in a solution containing phosphoric acid, and the product was reacted with 1-phenylpyrrolidone to give the dye.

Yield: 13.65 g

Melting point: 285° C.

Elemental analysis (calculated for C$_{22}$H$_{18}$O$_2$N$_4$S): calculated: C 65.66 H 4.51 N 13.92 found C: 65.90 H 4.62 N 13.48

Example 3

Preparation of 3

17.8 g (0.073 mol) of compound 1d were diazotized as in Examples 1 and 2 by means of nitrosylsulfuric acid in a solution containing phosphoric acid, and the product was then reacted with the thiazol

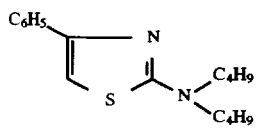

Yield: 12.8 g

Melting point: 226°–230° C.

Elemental analysis (calculated for C$_{29}$H$_{29}$O$_2$N$_5$S): calculated: C 64.06 H 5.38 N 12.88 found: C 64.10 H 5.44 N 12.40

The solvatochromism was investigated by recording UV spectra of solutions of the phenol derivatives 1, 2 and 3 in dioxane and dimethyl sulfoxide. The results are shown in the table. The measured wave number differences demonstrate the high hyperpolarizability.

| Phenol derivative | λmax [nm] in Dioxane | λmax [nm] in DMSO | $\Delta\tilde{\nu}$ [cm$^{-1}$] |
|---|---|---|---|
| 1 | 570 | 604 | 988 |
| 2 | 565 | 602 | 1088 |
| 3 | 588 | 605 | 478 |

Example 4

Preparation of 9

11.15 g (0.0242 mol) of compound 1 were dissolved in 100 ml of tetrahydrofuran, and 1.76 g (0.0267 mol) of malodinitrile, 5 ml of acetic acid, 2.5 ml of piperidine and 2.5 g of sodium sulfate were then added at room temperature. The mixture was refluxed for half an hour, cooled and then precipitated in water. The deep blue precipitate was isolated, dried and recrystallized from isobutanol.

Yield: 8.2 g

Melting point: 235°–236° C.

UV (CH$_2$Cl$_2$): $\lambda_{max}$=658 nm. $\epsilon$=69200 Elemental analysis (calculated for C$_{29}$H$_2$N$_6$O$_1$S$_1$) calculated: C 68.48 H 5.55 N 16.52 O 3.15 S 6.30 found: C 68.5 H 5.5 N 16.3 O 3.4 S 6.3.

Example 5

17 was prepared similarly to the preparation of 1:

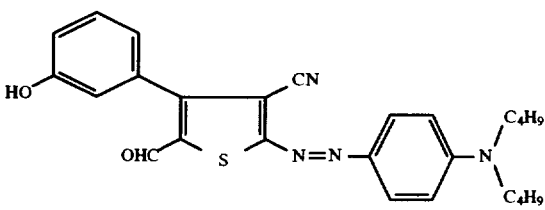

Melting point: 192°–193° C.

UV (CH$_2$Cl$_2$): $\lambda_{max}$=588 nm $\epsilon$=5100.

Example 6

18 was prepared by esterifying 17 with methacrylic acid:

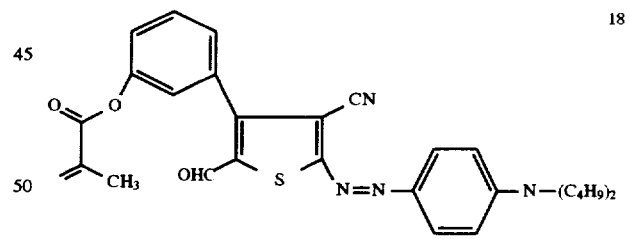

Example 7

19 was prepared similarly to the preparation of 9:

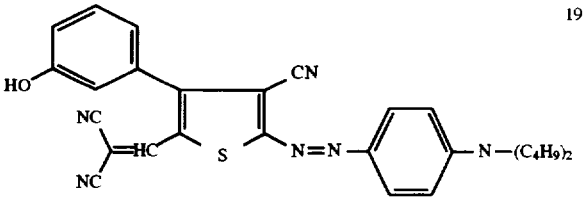

Example 8

20 was prepared by esterifying 19 with methacrylic acid:

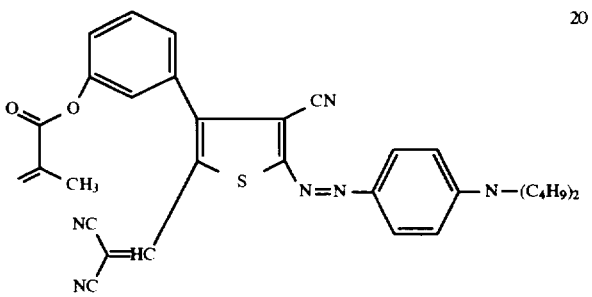

We claim:
1. A phenol derivative of the formula I

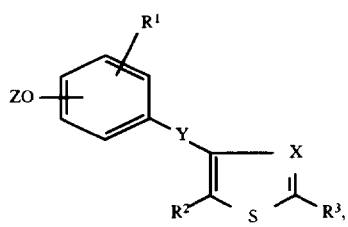

where

R$^1$ and R$^2$, independently of one another, are each hydrogen, C$_1$-C$_{10}$-alkyl, C$_3$-C$_8$-cycloalkyl, C$_1$-C$_{10}$-alkoxy, OH, NR$^5$R$^6$, CN, NO$_2$, halogen, CHO,

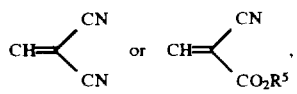

X is N or CR$^4$,
Y is a chemical bond, S,

SO$_2$, O or NR$^6$,
Z is hydrogen, acryloyl or methacryloyl,
R$^3$ is NH$_2$, N=N—G, where G is a heterocyclic coupling component, or

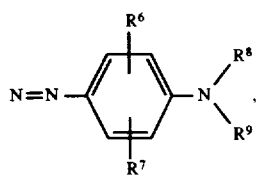

R$^4$ is hydrogen, CN, NO$_2$ or CO$_2$R$^5$,
R$^5$ is hydrogen, alkyl, cycloalkyl, unsubstituted or substituted phenyl, benzyl or alkoxy,
R$^6$ and R$^7$, independently of one another, are each hydrogen, C$_1$-C$_{10}$-alkyl, C$_3$-C$_8$-cycloalkyl or C$_1$-C$_6$-alkoxy which is unsubstituted or substituted by phenyl or by C$_1$-C$_4$-alkoxy, and
R$^8$ and R$^9$ are each hydrogen, alkyl, cycloalkyl or a crosslinkable group, or R$^8$ and R$^9$ together with the nitrogen atom linking them may form a ring with the proviso that if R$^3$ is NH$_2$, Y is a bond and R$^2$ is hydrogen, halogen or C$_1$-C$_{10}$-alkyl then Z is not hydrogen.

2. A phenol derivative as claimed in claim 1, wherein
R$^1$ is hydrogen, C$_1$-C$_{10}$-alkyl, C$_3$-C$_8$-cycloalkyl, C$_1$-C$_{10}$-alkoxy, OH, halogen or CHO and
R$^2$ is hydrogen, CN, NO$_2$, CHO,

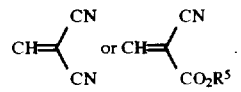

3. A phenol derivative as claimed in claim 1 wherein Y is a chemical bond.
4. A phenol derivative as claimed in claim 1 wherein X is CR$^4$.
5. A phenol derivative as claimed in claim 1 wherein R$^3$ is NH$_2$.
6. A phenol derivative as claimed in claim 3 of the formula II

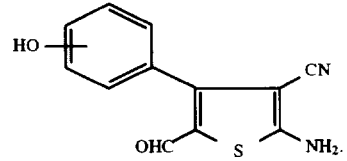

7. A phenol derivative as claimed in claim 1 wherein R$^3$ is N=N—G or

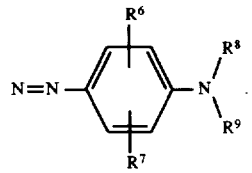

8. A process for the preparation of a phenol derivative of the formula I as claimed in claim 1 where R$^3$ is N=N—G or

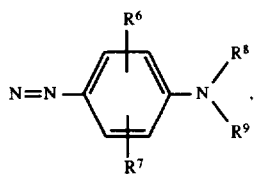

wherein a phenol derivative of the formula I where R$^3$ is NH$_2$ is diazotized and the product is reacted with a heterocyclic coupling component G or with

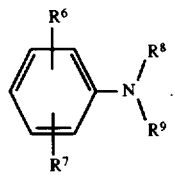

9. A nonlinear optical device comprising a polymer and the phenol derivative of claim 1.
10. A colored textile comprising a textile and the phenol derivative of claim 1.
11. A printing ink, comprising an ink base and the phenol derivative of claim 1.

* * * * *